United States Patent
Eckhardt

(10) Patent No.: US 10,101,326 B2
(45) Date of Patent: Oct. 16, 2018

(54) METHOD FOR DETERMINING A MARKER IN SMALL VOLUME OF A SAMPLE OF A BODILY FLUID

(75) Inventor: Florian Eckhardt, Berlin (DE)

(73) Assignee: B.R.A.H.M.S GMBH, Hennigsdorf (DE)

( * ) Notice: Subject to any disclaimer, the term of this patent is extended or adjusted under 35 U.S.C. 154(b) by 705 days.

(21) Appl. No.: 13/580,211

(22) PCT Filed: Feb. 22, 2011

(86) PCT No.: PCT/EP2011/052613
§ 371 (c)(1),
(2), (4) Date: Aug. 21, 2012

(87) PCT Pub. No.: WO2011/104238
PCT Pub. Date: Sep. 1, 2011

(65) Prior Publication Data
US 2012/0315665 A1 Dec. 13, 2012

(30) Foreign Application Priority Data
Feb. 23, 2010 (EP) .................... 10001817

(51) Int. Cl.
G01N 21/75 (2006.01)
G01N 33/558 (2006.01)
G01N 21/84 (2006.01)

(52) U.S. Cl.
CPC ....... *G01N 33/558* (2013.01); *G01N 21/8483* (2013.01)

(58) Field of Classification Search
CPC .................. G01N 21/8483; G01N 33/558
See application file for complete search history.

(56) References Cited

U.S. PATENT DOCUMENTS

| | | | |
|---|---|---|---|
| 5,602,040 A | 2/1997 | May et al. | |
| 5,889,585 A * | 3/1999 | Markart | 356/39 |
| 6,187,598 B1 | 2/2001 | May et al. | |
| 6,228,660 B1 | 5/2001 | May et al. | |
| 6,551,842 B1 | 4/2003 | Carpenter | |
| 6,818,455 B2 | 11/2004 | May et al. | |
| 7,109,042 B2 | 9/2006 | May et al. | |
| 7,521,259 B2 | 4/2009 | Petruno et al. | |
| 9,360,478 B2 | 6/2016 | Abbott | |
| 2001/0008774 A1 | 7/2001 | May et al. | |
| 2001/0041368 A1 | 11/2001 | May et al. | |
| 2003/0054567 A1 | 3/2003 | Miyoshi | |
| 2003/0206302 A1 * | 11/2003 | Pugh | 356/436 |
| 2005/0244986 A1 | 11/2005 | May et al. | |
| 2007/0231922 A1 * | 10/2007 | Petruno et al. | 436/514 |
| 2010/0041154 A1 | 2/2010 | Ohman et al. | |
| 2010/0104475 A1 | 4/2010 | Miyoshi et al. | |
| 2010/0137145 A1 | 6/2010 | Qinwei | |
| 2010/0197000 A1 | 8/2010 | Qinwei | |
| 2011/0003320 A1 | 1/2011 | Ito | |

FOREIGN PATENT DOCUMENTS

| | | |
|---|---|---|
| CN | 1392953 A | 1/2003 |
| CN | 1936540 A | 3/2007 |
| CN | 101213451 A | 7/2008 |
| EP | 2251690 B1 | 1/2016 |
| JP | 2003-04743 A | 1/2003 |
| JP | 2008-147551 A | 6/2008 |
| JP | 2009-210505 A | 9/2009 |
| JP | 2010-19610 A | 1/2010 |
| WO | 2007/149043 A1 | 12/2007 |
| WO | 2008-155579 A1 | 12/2008 |

OTHER PUBLICATIONS

International Search Report, dated Apr. 14, 2011, issued in corresponding PCT/EP2011/052613.
Written Opinion, dated Apr. 14, 2011, issued in corresponding PCT/EP2011/052613.
English Abstract: Bibliographic data: CN1936540 (A)—Mar. 28, 2007.
Statmark (TM) Flu A/B, Mar. 2005—2 pages.
Flu Virus Kit, Statmark TM Flu Stick AB, Credited in Oct. 2007, Revised Jan. 2009 (Third Edition), URL: https://www.pmda.go.jp/PmdaSearch/ivdDetail/ResultDataSetPDF/531143_21900AMX01766000_B_02_01, with partial translation—5 pages.

* cited by examiner

*Primary Examiner* — Lisa J Hobbs
(74) *Attorney, Agent, or Firm* — Millen White Zelano and Branigan, PC; John Sopp

(57) ABSTRACT

The invention refers to a method for determining a marker in a small volume of a sample of a bodily fluid, the method comprising the steps of: providing a flow test element having a plurality of functional zones (3, 4, 5, 6, 7), the plurality of functional zones (3, 4, 5, 6, 7) being at least partially fluidly connected and comprising an application zone (3) and a testing zone (5) fluidly connected to the application zone (3) and configured for determination of a marker in a bodily fluid and/or a constituent of the bodily fluid, applying a small volume of a liquid sample to the sample application zone (3) of the flow test element, determining a correct test performance, wherein the step of determining correct test performance comprises the steps of measuring at least one optical parameter for one or more functional zones (3; 4; 5; 6; 7), comparing the at least one optical parameter measured to at least one predefined optical parameter assigned to the one or more functional zones (3; 4; 5; 6; 7), and, if the correct test performance is determined, determining the marker in the liquid sample by reading the testing zone (5). Also, a method for determining a correct test performance for a flow test element is provided.

11 Claims, 2 Drawing Sheets

METHOD FOR DETERMINING A MARKER IN SMALL VOLUME OF A SAMPLE OF A BODILY FLUID

Figure 1:
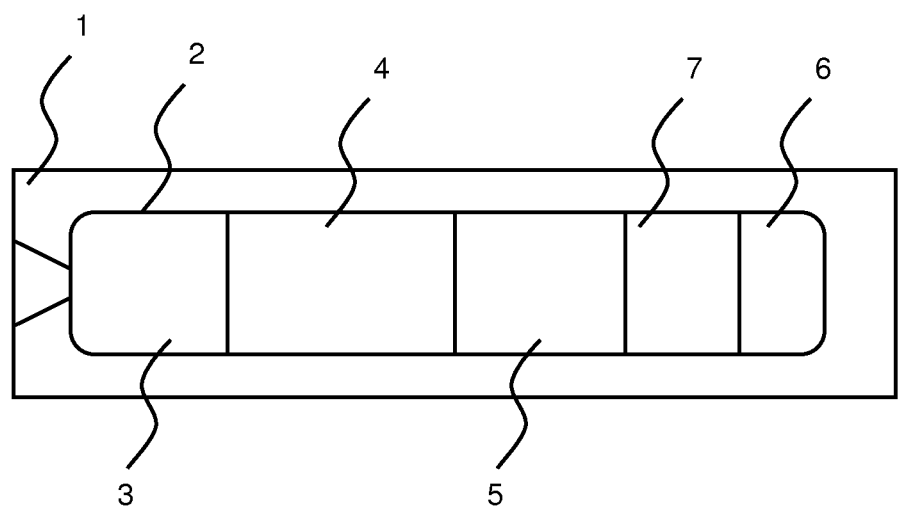

The invention refers to a method for determining a marker in a small volume of a sample of a bodily fluid.

BACKGROUND OF THE INVENTION

Such methods are used for rapidly determining the presence of one or more markers in a small volume of a bodily fluid. Known methods and devices are, for example, disclosed in the following documents: WO 2004/033101 A1, WO 2007/000048 A1, and WO 2009/14360 A1.

WO 2007/000048 A1 describes a point-of-care device comprising three or more porous membranes used to detect one or more markers from a small sample of fluid useful for identifying markers from whole blood. Arrays are described comprising a first step membrane being retardant of red blood cells and containing a detection reagent and a second step membrane having a porosity that is further retardant of red blood cells compared to said first step with minimal hemolysis of the sample and a third step membrane having a lower porosity than said second step and containing a capture probe.

Document US 2005/0244986 A1 discloses an analytical test device useful for example in pregnancy testing. In operation, a liquid sample is applied to a bottom end of the test device. There are functional zones provided on the test device. A circular zone may act as a control giving rise, for example, to a colored signal irrespective of whether or not the liquid sample applied contains the analyte to be determined. The determination of the analyte takes place in another circular zone. The user can determine whether the analyte is present in the liquid sample applied by comparing the signal produced in the two zones.

Document WO 2007/149043 A1 discloses an assay device for performing an assay on a liquid sample using a detection conjugate capable of binding to an antigen and containing a label.

Document US 2009/0253119 A1 relates to a lateral flow assay and system, including a test strip, for detection and quantification of analytes in samples, such as samples containing cells and fluid.

Document EP 1 975 619 A1 provides a chromatographic test device, comprising a first blood cell separation member, a second blood cell separation member and a chromatographic carrier disposed in this order from the upstream side of the direction of development of a sample.

SUMMARY OF THE INVENTION

It is the object of the invention to provide an improved method for determining a marker in a small volume of a sample of a bodily fluid, wherein a non correct use of a flow test element used to for determination of the marker is avoided.

This object is solved by a method for determining a marker in small volume of a sample of a bodily fluid according claim 1. Further, a method for determining a correct test performance for a test flow element according claim 1 is provided. Advantages developments of the invention are disclosed in dependent claims.

In the course of the optical determination one or more spectroscopic parameters selected from the following group of spectroscopic parameters may be measured: absorption, fluorescence, reflection, remission, and transmission.

One or more of the functional zones on the flow test element may be provided with two or more functional sub-zones. For example, a plurality of testing sub-zones may be located on the flow test element.

By determining the correct test performance, for example, it is avoided that a liquid sample is applied to the flow test element for which the test element is not configured. The flow test element may be configured for a bodily fluid and/or a constituent of the bodily fluid. As used herein, the term "constituent" has to be distinguished from a substance which would be added to the bodily fluid subsequently. The added substance may also be referred to as an admixture or an admixed substance. In case of a bodily fluid, such substance, for example, could be added to the bodily fluid after taking it from a patient, e.g. an antibody could be added. In contrast, the constituent as defined here is part of the bodily fluid itself. Examples for constituents of a whole blood sample are blood serum and blood plasma.

If, for example, a liquid sample is applied to the flow test element for which the flow test element is not configured, this will lead to erroneous results. The proposed method ensures that the determination of the marker in the liquid sample is performed correctly. This is because, there is a step of determining the correct test performance which gives the user the information whether the correct test performance is provided, for example, whether the correct liquid was applied to the flow test element.

Preferably, the determination of the marker in the liquid sample by reading the testing zone is done by optical testing using one or more testing wavelengths. In a preferred embodiment, the step of determining the correct test performance is performed by optical determination using one or more wavelengths which are different from the testing wavelength(s). For example, a fluorescence and/or an absorption wavelength may be selected which is different from the testing wavelength(s).

As used herein "fluidly connected" means that fluids, such as for instance the sample may pass from one compartment or part of the device according to the present invention essentially unhindered. Such feature, preferably, is independent of real presence of a liquid sample.

The step for determining the correct test performance, especially for correct sample use, may be repeated once or several times after a first determination during the time between application of the sample liquid to the flow test element and determination of the marker. Even after determination of the marker, testing for correct test performance may be performed, preferably as an additional step of determination. The step may be performed for the purpose of determining correct test performance, especially correct sample use, for or in one or more functional zones.

The step of determining the correct test performance may be performed at one of the functional zones after a part of the applied liquid reaches the one functional zone. In this case the at least one optical parameter measured for the one functional zone is compared to one or more predefined optical parameters assigned to the one functional zone.

In general, as used herein "measured for the one functional zone" means that the parameter was measured for characterizing the one functional zone. The optical measurement may be performed at an area within the one functional zone and/or an area located outside the one functional zone.

The one testing zone ore the plurality of testing sub-zones may be configured for determination of one or more markers. Examples of markers which may be determined by the method provided are described in the following.

Procalcitonin (PCT) has become a well-established biomarker for sepsis diagnosis: PCT reflects the severity of bacterial infection and is in particular used to monitor progression of infection into sepsis, severe sepsis, or septic shock. It is possible to use PCT to measure the activity of the systemic inflammatory response, to control success of therapy, and to estimate prognosis (Assicot M et al.: Lancet 1993, 341:515-8; Clec'h C et al.: Diagnostic and prognostic value of procalcitonin in patients with septic shock. Crit Care Med 2004; 32:1166-9; Lee Y J et al, Yonsei Med J 2004, 45, 29-37; Meisner M Curr Opin Crit Care 2005, 11, 473-480; Wunder C et al. Inflamm Res 2004, 53, 158-163). The increase of PCT levels in patients with sepsis correlates with mortality (Oberhoffer M et al. Clin Chem Lab Med 1999; 37:363-368).

The peptide Adrenomedullin (ADM) was first described in 1993 (Kitamura et al. (1993), Biochem. Biophys. Res. Commun. 192:553-560) as a novel hypotensive peptide comprising 52 amino acids, which had been isolated from a human pheochromocytoma. In the same year, cDNA coding for a precursor peptide comprising 185 amino acids and the complete amino acid sequence of this precursor peptide were also described (Kitamura et al. (1993), Biochem. Biophys. Res. Commun 194:720-725). The precursor peptide, which comprises, inter alia, a signal sequence of 21 amino acids at the N-terminus, is referred to as "pre-pro-Adrenomedullin" (pre-pro-ADM). The ADM peptide comprises amino acids 95 to 146 of pre-pro-ADM, from which it is formed by proteolytic cleavage. Some peptide fragments of those formed in the cleavage of the pre-proADM have been characterized in detail, in particular the physiologically active peptides adrenomedullin (ADM) and "PAMP", a peptide comprising 20 amino acids (22-41) which follow the 21 amino acids of the signal peptide in pre-Pro-ADM. Another fragment of unknown function and high ex vivo stability is midregional proAdrenomedullin (MR-proADM) (Struck et al. (2004), Peptides 25(8):1369-72), for which a reliable quantification method has been developed (Morgenthaler et al. (2005), Clin. Chem. 51(10): 1823-9). ADM is an effective vasodilator. The hypotensive effect has been associated particularly with peptide segments in the C-terminal part of ADM. Peptide sequences of the N-terminus of ADM on the other hand exhibit hypertensive effects (Kitamura et al. (2001), Peptides 22, 1713-1718).

Endothelin (ET)-1 is a potent endothelium-derived endogenous vasoconstrictor (Yanagisawa M, Kurihara H, Kimura S, Goto K, Masaki T, J Hypertens Suppl 1988; 6:S188-91.). ET-1 exerts its vascular effects by activation of ET(A) and ET(B) receptors on smooth muscle cells, which causes an increase in intracellular calcium (Yanagisawa et al, J Hypertens Suppl 1988; 6:5188-91). Mature Endothelin-1 is derived from a larger precursor termed Pro-Endothelin-1. Pro-Endothelin-1 can be proteolytically processed into various fragments as described (Struck J, Morgenthaler N G, Bergmann Peptides. 2005 December; 26(12):2482-6.). These fragments are subject to proteolytic degradation in the blood circulation, which can happen quickly or slowly, depending on the type of fragment and the type and concentration/activity of proteases present in the circulation. One example of these fragments is C-terminal pro-Endothelin-1 (CT-proET-1), which can be measured by a sandwich immunoassay (Papassotiriou J, Morgenthaler N G, Struck J, Alonso C, Bergmann A. Clin Chem. 2006 June; 52(6):1144-51.).

B-type natriuretic peptides (BNP) are quantitative markers of heart failure. The use of B-type natriuretic peptide (BNP) and its amino-terminal fragment, N-terminal pro-B-type natriuretic peptide (NT-proBNP) significantly increases the diagnostic accuracy in the ED [Januzzi, J. L., Jr., et al., Am J Cardiol, 2005. 95(8): p. 948-54; Maisel, A. S., et al., N Engl J Med, 2002. 347(3): p. 161-7], and thereby improves patient evaluation and treatment [Moe, G. W., et al., Circulation, 2007. 115(24): p. 3103-10; 8. Mueller, C., et al., N Engl J Med, 2004. 350(7): p. 647-54.]. The concentration of atrial natriuretic peptide (ANP) in the circulation is approximately 50- to 100-fold higher than BNP [Pandey, K. N., Peptides, 2005. 26(6): p. 901-32]. Therefore, the biological signal reflected by the increased ANP may be pathophysiologically and therefore diagnostically even more important than the signal of BNP. Despite this, little is known about the diagnostic performance of ANP and its precursors [Cowie, M. R., et al., Lancet, 1997. 350(9088): p. 1349-53]. Mature ANP is derived from the precursor N-terminal-proANP (NT-proANP), which is significantly more stable in the circulation than the mature peptide and is therefore thought to be a more reliable analyte [Vesely, D. L., IUBMB Life, 2002. 53(3): p. 153—Pandey, K. N., Peptides, 2005. 26(6): p. 901-32].

Atrial natriuretic peptide (ANP), a member of the natriuretic peptide family, regulates several physiological parameters including diuresis and natriuresis, and lower arterial blood pressure (BP). It is predominantly produced in the atrium of the heart and comprises 98% of natriuretic peptides in the circulation. (Vesely D L. Life 2002; 53:153-159) ANP is derived from the cleavage of its precursor prohormone, which is significantly more stable in the circulation than the mature peptide. A midregional fragment of the precursor hormone (amino acids 53-90 of NT-proANP), called midregional-proANP (MR-proANP), may be relatively resistant to degradation by exoproteases, unlike epitopes in the N- or C-terminals of proANP used in previous immunoassays. (Morgenthaler N G et al. Clin Chem 2004; 50:234-236; Gerszten R E et al. Am J Physiol Lung Cell Mol Physiol 2008).

Myoglobin is a single-chain globular protein of 153 amino acids, containing a heme (iron-containing porphyrin) prosthetic group in the center around which the remaining apoprotein folds. Myoglobin is a sensitive marker for muscle injury, making it a potential marker for heart attack in patients with chest pain. (M. Weber, M. Rau, K. Madlener, A. Elsaesser, D. Bankovic, V. Mitrovic and C. Hamm (2005) Clinical Biochemistry 38: 1027) CK-MB and cardial troponin T cTnT is used in combination with ECG, and the clinical signs to diagnose Acute Myocardial Infarction (AMI). Cardial Troponin is a protein complex consisting of the three subunits T (cTcT), I (cTcI) and C, of which T and I are only located in heat muscle tissue and are used as markers for diagnostic purposes (Rottbauer W et al., Eur Heart J 1996; 17:3-8).

Arginine vasopressin (AVP), also known as vasopressin, argipressin or antidiuretic hormone (ADH), is a hormone found in most mammals, including humans (Caldwell H K, Young W S III (2006). in Lajtha A, Lim R. Handbook of Neurochemistry and Molecular Neurobiology: Neuroactive Proteins and Peptides (3rd edition ed.). Berlin: Springer. pp. 573-607. ISBN 0-387-30348-0). Vasopressin is a peptide hormone. It is derived from a preprohormone precursor that is synthesized in the hypothalamus and stored in vesicles at the posterior pituitary. Decreased vasopressin release or decreased renal sensitivity to vasopressin leads to diabetes insipidus, a condition featuring hypernatremia (increased blood sodium concentration), polyuria (excess urine production), and polydipsia (thirst).

As used herein, terms such as "determining (a) marker(s)" and the like include the detection of the presence or absence and/or quantification of the amount and/or concentration of the marker(s) in a sample. Hereby, presence or absence is to be understood in view of the detectable presence of the marker, i.e. of the detection limit of the assay.

"Markers" are substances indicative of physiological or pathological conditions. They include, for example, cardiac analytes which are proteins released from myocardial cells into circulation due to deterioration of cardiac tissue, hormones indicative of pregnancy, glucose used to monitor a diabetic condition and various proteins or toxins resulting from infections.

In certain embodiments, a marker is a protein or peptide which is to be detected and/or quantified with the arrays, devices, methods and uses of the present invention. This includes fragments of a length of at least 12 amino acids, preferably at least 15 amino acids of said proteins or peptides. Specific examples of such proteins or peptides in accordance with the present invention are markers associated with the diagnosis and/or prognosis of cardiovascular events such as myoglobin, troponins T (cTnT) and I (cTnI), creatinine kinase MB (CK-MB), FABP, GDF-15, ST-2, procalcitonin (PCT), C-reactive protein (CRP), proAdrenomedullin and fragments thereof including midregional pro-adrenomedullin (MR-proADM), Adrenomedullin, PAMP, C-terminal proAdrenomedullin (CT-proADM), proEndothelin-1 and fragments thereof including C-terminal pro-endothelin-1 (CT-proET-1), big-Endothelin-1, Endothelin-1, NT-proEndothelin-1, proANP and fragments thereof including midregional pro-atrial natriuretic peptide (MR-proANP), N-terminal proANP (NT-proANP), ANP, proVasopressin and fragments thereof including C-terminal pro-arginine vasopressin peptide (CT-proAVP, "Copeptin"), Vasopressin, Neurophysin II, proBNP and fragments thereof including BNP and N-terminal proBNP (NT-proBNP).

It is to be understood that the marker proteins and/or peptides described herein, encompass fragments of said marker proteins and/or peptides of at least 12 amino acids, preferably at least 15 amino acids in length are encompassed as markers.

Furthermore, hormones associated with pregnancy or ovulation such as human chorionic gonadotropin (hCG) and luteinizing hormone (LH), respectively may also be detected using this invention or various embodiments thereof. It is also within the scope of this invention that other antigens for diseases such as cancer, specifically prostate cancer antigens (prostate serum antigen, PSA) may also be detected using this invention. Additional applications of this invention include the recognition of markers associated with viral infections such as hepatitis, bacterial and fungal infection including *Helicobacter pylori* for gastrointestinal ulcers, other infections caused by *Bacillus anthracis, Pediculus humanis, Siphonaptera* and gram positive bacteria as *Streptococcus pyogenes, Streptococcus pneumoniae* and *Streptococcus faecalis* are all non-limiting examples. This invention may also be useful for detecting drugs including drugs of abuse. Enzymatic assays such as those that determine levels of glucose and in blood are also contemplated by the present invention. It will be recognized that the use of the devices is not limited to these specific markers or, indeed, to whole blood but is equally applicable to other analytical procedures such as those mentioned above.

In a preferred embodiment, the step of determining the correct test performance comprises a step of determining correct sample use by optically determining whether the applied liquid sample is a bodily fluid or a constituent of the bodily fluid, the test flow element being configured for determination of the marker in the bodily fluid or the constituent of the bodily fluid.

According to a preferred embodiment, the method further comprises steps of applying a small volume of a whole blood sample, and optically determining whether the whole blood sample is non hemolysed or hemolysed blood. In a preferred embodiment, the optical determination comprises a step of measuring a remission signal for light irradiated into an area of interest on the flow test element. The measured remission signal may be compared with a reference signal for determining whether non hemolysed or hemolysed blood is present. As used herein, "whole blood sample" specifies an unprocessed or essentially unprocessed blood sample.

In another preferred embodiment, the step of measuring comprises a step of optically measuring an area fluidly connected to and located between the testing zone and the control zone. Because the area investigated in this case is located downstream of the testing zone the optical measurement gives information about the part of the liquid sample which entered the testing zone before.

In a preferred embodiment, the step of providing the flow test element comprises a step of providing a flow test element having a bridging zone located between and fluidly connected to the application zone and the testing zone, and a control zone located upstream from and fluidly connected to the testing zone. The bridging zone may be provided by a bridge membrane fluidly connected to the application zone and the testing zone. The bridge membrane may have an average pore dimension of 8.0 μm+/−2 nm and a capillary flow for serum or plasma at a distance of 2 cm of less than 30 seconds and/or at a distance of 4 cm of less than 180 seconds, wherein the capillary flow for serum or plasma in the bridge membrane is lower than in the first porous material and higher than in the testing zone. Also, the testing zone, and the control zone may be implemented by one or more membranes. Preferably, the membranes are made of a porous material.

According to a further embodiment, the step of determining the correct test performance comprises a step of optically measuring at least one of the functional zones selected from the following group of functional zones: the application zone, the bridging zone, the detection zone, and the control zone.

In a further embodiment, the step of determining correct test performance comprises a step of optically measuring an area of the flow test element located outside of the plurality of functional zones. Such measurement may be performed as an alternative or in addition to the measurement within one of the functional zones. For example, the optical measuring may be performed for areas of the flow test element located between two of the functional zones. An optical measurement with respect to the correct liquid in one of the functional zones may be performed for an area located upstream and/or downstream of a functional zone of interest.

In a preferred embodiment, the method further comprises steps of applying a small volume of a whole blood sample, and optically determining erythrocyte leakage into an area of interest on the flow test element. If, for example, a marker shall be determined in a whole blood sample, it usually needs to be avoided that erythrocytes leak into the testing zone itself. By the above embodiment it can be checked whether such leakage happened or not. If the step of determining correct test performance indicates that such leakage happened, this gives the information to the user that measurement results collected under those circumstances may not be correct.

According to a further embodiment, the step of determining the correct test performance comprises a step of performing a plurality of optical measurements at different times. The plurality of optical measurements may be performed for the same area or different areas of interest on the flow test element.

In another embodiment, the step of determining the marker comprises at least one of the following steps: determining the presence of the marker in the liquid sample, and determining the concentration of the marker in the liquid sample.

In still another preferred embodiment, the step of determining the correct test performance comprises a step of optically determining whether the applied liquid sample is a bodily fluid or a constituent of a bodily fluid selected from the following group: a whole blood sample, a blood serum sample, a blood plasma sample, a urine sample, a cerebrospinal fluid sample, a stool sample, a saliva sample, and a lymph sample.

According to another aspect of the invention, a method for determining a correct test performance for a flow test element is provided, the method comprising the steps of:
providing a flow test element having a plurality of functional zones, the plurality of functional zones being at least partially fluidly connected and comprising an application zone and a testing zone fluidly connected to the application zone and configured for determination of a marker in a bodily fluid and/or a constituent of the bodily fluid,
applying a small volume of a liquid sample to the sample application zone of the flow test element,
determining a correct test performance, wherein the step of determining correct test performance comprises the steps of measuring at least one optical parameter for the functional zone, and comparing the at least one optical parameter measured to at least one predefined optical parameter assigned to the one or more functional zones.

If in the step of determining the correct test performance non-correct test performance is detected, it may be provided that the analyzing system is interrupting further analysis. For example, the analyzing system may be blocked as to further use of the flow test element to which the liquid sample was applied. In a preferred embodiment, a warning signal is presented to the user of the analyzing system. The warning signal may comprise at least one of an acoustic signal and a video signal.

DESCRIPTION OF PREFERRED EMBODIMENTS OF THE INVENTION

Following the invention will be described in further detail by way of example with reference to different embodiments. In the figures, FIG. 1 shows a schematic representation of a flow test element in a top view, and FIG. 2 shows spectroscopic remission signals (relative units) in dependence on the position along a test flow element (relative units) provided with a whole blood sample at different incubation times.

The following examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

Figure 2:
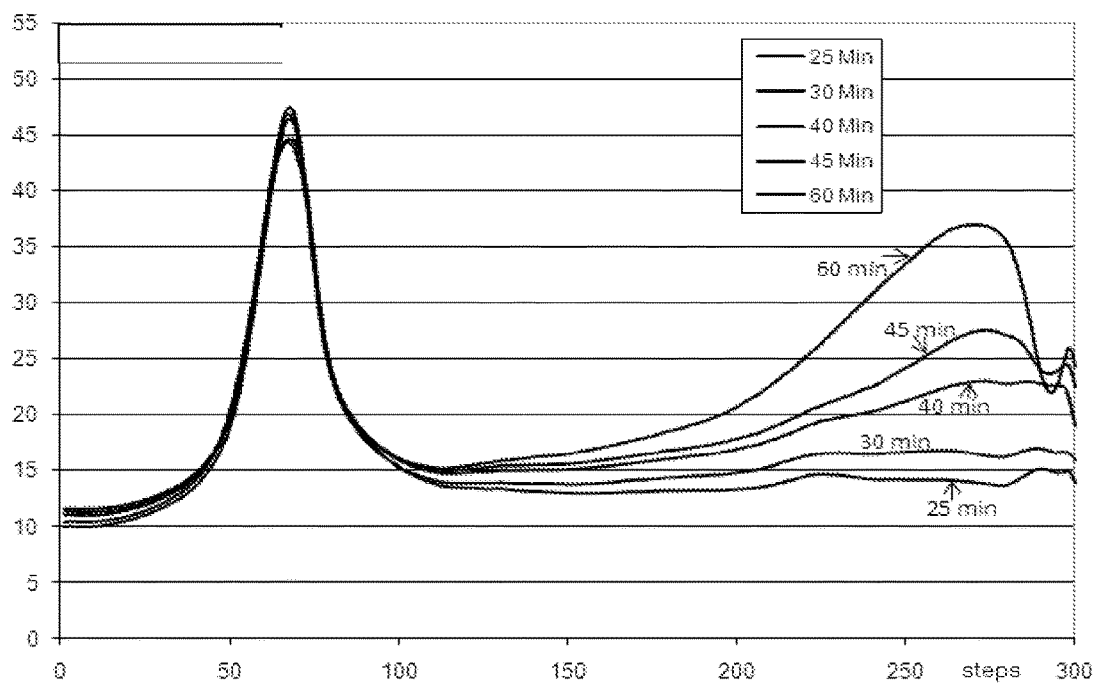

FIG. 1 shows a schematically flow test element in a top view. The flow test element which may also referred to as a point-of-care device, comprises a device body 1 receiving a membrane body 2 on which a plurality of functional zones are implemented. The functional zones fluidly connected, comprise the following zones: application zone 3, a bridging zone 4, testing zone 5, and control zone 6.

A "point of care" (POC) test is defined as any diagnostic test performed at or near the site of patient care (Kost, Goals, guidelines and principles for point-of-care testing. In: Kost G J, ed. Principles and practice of point-of-care testing. Philadelphia: Lippincott Williams and Wilkins. 2002, Chapter 1, pp 3-12). By bringing the analysis closer to the patient, several process steps have been eliminated, facilitating a shorter time to result and faster management response with improved outcomes. The advantages of POC tests are faster turn-around-times (TAT), more rapid medical decisions, avoidance of long sample transport and the need of only small specimen volumes (Heinschink et al., Point-of-care testing. Laboratoriums Medizin 2002. 26 (1-2): 61-67.)

The application zone 3 is configured to receive a small volume of a bodily fluid which then at least partially will flow in the membrane body 2 to the testing zone 5 and the control zone 6, respectively. As used herein "sample application zone" specifies a part of the device where the sample is applied, which may for instance by immersing the sample application zone into the sample or by applying the sample with a sample transfer means such as a syringe or pipette. The sample application zone is thus an opening in the device which may for instance be in the form of a pocket or indentation through which the sample can be applied to the first porous material.

The flowing takes place along a sample flow channel formed between the application zone 3 and the control zone 5. The membrane body 2 may be provided with one or more membrane elements which in one embodiment are provided in a stack of membranes. Flow channels provided by the porous membrane material have dimensions that allow capillary flow.

In one embodiment the testing zone 4 is configured for the determination of the presence of a marker in a whole blood sample. The flow test element may be used as follows.

As is readily apparent, upon contact with a first porous material provided within and/or adjacent to the application zone 3, the red blood cells of the applied sample will begin to separate from plasma and in the course of its flow the marker will encounter a detection reagent, typically but not limited to a labeled antibody directed to an epitope of the marker to form a marker-detection reagent complex. In the embodiment described, the marker-detection reagent complex then moves to the bridge zone 4 provided by the bridge membrane, where red blood cell migration will be further hindered/retarded. The marker-detection reagent complex then moves toward the testing zone 5 provided by a testing membrane and encounters an immobilized capture probe, typically but not limited to an antibody directed to a separate epitope of the marker or to an epitope of the detection reagent. The reaction of the marker-detection reagent complex with the immobilized capture probes forms a concentrated capture spot visible to the naked eye or appropriate instrumentation. The optional control zone 6 downstream of the capture spot in the testing zone 5 will contain the control reagent. In preferred embodiments, the control reagent may be an anti-animal IgG. Alternatively, in place of the control zone 6, variations in the length of the transparent cover tape over the membranes of the testing device can cause the sample, when it reaches the end of the testing membrane to evaporate in a controlled manner revealing a readily detectable signal.

It is within the scope of the present invention to detect a marker or even multiple markers in the fluid sample at one time. Accordingly, it will be appreciated by one skilled in the art that one or more detection reagents and/or one or more capture probes can be deposited on the point-of-care device of the present invention.

In principle, the assay, i.e. the combination of detection reagent and capture probe used for detection of the marker can be based on any type applied in the field of diagnostics. The assays can be non-competitive assays, i.e. sandwich assays, or competitive assays (The Immunoassay Handbook, Ed. David Wild, Elsevier LTD, Oxford; 3rd ed. (May 2005), ISBN-13: 978-0080445267; Hultschig C et al., Curr Opin Chem Biol. 2006 February; 10(1):4-10. PMID: 16376134).

As used herein, a capture probe may be selected from the group comprising a nucleic acid molecule, a carbohydrate molecule, a PNA molecule, an aptamer, a protein, an antibody, a peptide or a glycoprotein, preferably an antibody.

Any of a variety of labelling of capture probes and corresponding detection systems in the testing device available to the skilled artisan may be utilized. Known labels include but are not restricted to metal, fluorescence, electrochemilumenscence and enzyme labels. Metal labels are especially preferred due to their remarkable sensitivity. Amongst the metals, gold is most preferred principally because it is widely employed for this type of reaction and its characteristics are well understood.

In certain embodiments the first porous material comprises antibody-gold particle-conjugates which bind to the marker to be determined in the whole blood sample. It is to be understood hereby, that the antibody-gold particle-conjugates are located as such in the first porous material and that the antibody-gold particle-conjugates will upon contact with the sample be suspended in the sample and transported together with the sample. Thus, it is obvious that the antibody-gold particle-conjugates may not be irreversibly immobilized in the first porous material. However, an immobilization of the antibody-gold particle-conjugates on the first porous material, which is reversible upon contact with the sample, e.g. which is susceptible to hydrolysis, may be implemented in certain embodiments.

The preferred particle size for gold labeled antibodies employed is from about 20 to 65 nm, although appreciable variation can be tolerated depending on well understood factors such as the clinical cut off of the marker and the affinity of the reactants. Additionally, a gold signal can be enhanced to become readily visible by the use of reducible silver salt which deposits as visible product. A typical reactive salt is silver lactate, which serves as the source of reducible silver ions, employing hydroquinone as a reducing agent. The metallic silver forms a readily discernible black deposit around each particle of gold. Alternatively, if an enzyme label such as horseradish peroxidase is employed, the reaction may be detected by the addition of hydrogen peroxide and a dye such as CIS ortho phenylenediamine in accordance with standard procedures. Additional labels that may be used well within the scope of this invention are paramagnetic labels as described in U.S. Pat. No. 6,046,585 (which is incorporated herein by reference in its entirety) which enable an even greater sensitivity for marker detection.

In the context of the present application "detecting reagent" is a material, often an antibody to the marker, which is to be detected in the liquid sample. In certain embodiments it is releasably bound to the first porous material carrier at or downstream of the application point for the liquid sample. For most immunochemical analyses, it is labeled with a detectable label such as colloidal gold and forms a complex with the marker to be determined.

In the context of capillary flow of serum of the bridge membrane, the term "horizontal variation" specifies a variation of the flow rate in the direction of the flow of the serum.

As used herein "separating serum from blood cells" means that blood cells, in particular red blood cells are retained, whereas the serum passes on to the adjacent compartment or part of the device, such as to the next membrane. Hereby, preferably at least 95%, more preferably at least 99%, even more preferably at least 99.5% most preferably about 100% of the red blood cells are retained.

The method for determining the presence of a marker in a bodily fluid described by reference to the above non limiting embodiments comprises a step of determining correct sample use. This is done by (a) spectroscopic measurement(s). One or more spectroscopic parameters selected from the group comprising absorption, fluorescence, transmission, reflection, and remission is detected and analyzed for determining whether a part of a liquid sample applied to the application zone 3 and reaching one of the functional zones on the flow test element is one of the bodily fluid for which the flow test element is configured and a constituent of the bodily fluid. Preferably, area 6 is optically investigated for determination of correct sample use. For example, an area 7 located between the testing zone 5 and the control zone 6 may be optically investigated for determination what kind of liquid sample reached the testing zone 5 and/or the control zone 6. For example, the optical parameter remission may be analyzed for the area 7.

In a preferred embodiment, the method described above comprises the steps of applying a small volume of a whole blood sample, and optically determining erythrocyte leakage into an area of interest on the flow test element. If, for example, a marker shall be determined in a whole blood sample, it usually needs be avoided that erythrocyte leak into the testing zone 5 itself. By the above embodiment it can be checked whether such leakage happened or not. If the step of determining correct sample usage indicates that such leakage happened, this gives the information to the user that measurement results collected under those circumstances may not be correct.

FIG. 2 shows spectroscopic remission signals (relative units) in dependence on the relative position on the flow test element 1 (relative units) provided with a whole blood sample at different incubation times. The flow test element 1 (see FIG. 1) is scanned from left to right covering at least the control zone 6, the area 7 and the test zone 5. On the left hand side a so-called control band assigned to the remission signal in the control zone 6 does not change over time. An increase of the remission signal on the right hand side indicates erythrocyte leakage into the testing zone 5 on the flow test element 1.

The features disclosed in at least one of the specification, the claims, and the figures may be material for the realization of the invention in its various embodiments, taken in isolation or in various combinations thereof.

The invention claimed is:

1. A method for determining correct use of a flow test element, comprising:
   providing a flow test element having a plurality of functional zones (3, 4, 5, 6, and optionally 7), the plurality of functional zones (3, 4, 5, 6, and optionally 7) being at least partially fluidly connected and comprising an application zone (3), a bridging zone (4), a testing zone (5) fluidly connected to the application zone (3) and configured for determination of a marker in a whole blood sample, a control zone (6) and optionally an optional sample determination zone (7), wherein the bridging zone (4) is located between and fluidly connected to the application zone (3) and the testing zone (5), and wherein the bridging zone (4) comprises a bridge membrane fluidly connected to the application zone (3) and the testing zone (5) configured to hinder migration of erythrocytes to the testing zone (5), and applying a small volume of a whole blood sample to the sample application zone (3) of the flow test element and determining if the flow test element is being correctly used by:

(a) measuring at least one optical parameter for one or more of the functional zones (3; 4; 5; 6; 7), and (b) comparing the at least one optical parameter determined in (a) to at least one predefined optical parameter assigned to the one or more functional zones (3; 4; 5; 6; 7), thereby optically determining whether a part of the applied whole blood sample reaching one of the zones of the plurality of functional zones (3, 4, 5, 6, 7) is a whole blood sample;

wherein the method includes:

making an optical determination in control zone (6) of whether the correct sample material was used, and optionally making an optical determination of a marker in the sample in testing zone (5).

2. The method according to claim 1, wherein:

the optically determining step is for determining whether a part of the whole blood sample reaching the testing zone (5) is non hemolysed or hemolysed blood.

3. The method according to claim 1, wherein the step of measuring comprises a step of optically measuring an area fluidly connected to and located between the testing zone (5) and the control zone (6).

4. The method according to claim 1, wherein the step of providing the flow test element comprises a step of providing a flow test element having at least one of a bridging zone (4) located between and fluidly connected to the application zone (3) and the testing zone (5), and a control zone (6) located upstream from and fluidly connected to the testing zone (5); the fluid connections being by flow channels between the zones which allow capillary flow.

5. The method according to claim 1, wherein the step of determining the correct use of the flow test element further comprises a step of optically measuring an area of the flow test element located outside of the plurality of functional zones (3, 4, 5, 6, 7).

6. The method according to claim 1, wherein:

the optically determining step is for determining erythrocyte leakage into an area of interest on the flow test element.

7. The method according to claim 1, wherein the step of determining the correct use of the flow test element comprises performing a plurality of optical measurements at different times.

8. The method according to claim 1, wherein the step of determining the marker in the whole blood sample in testing zone (5) comprises at least one of the following steps:

determining the presence of the marker in the sample, and determining the concentration of the marker in the sample.

9. The method according to claim 1, wherein a step of optical determination of a marker in the sample in the testing zone (5) is performed.

10. A method according to claim 1, wherein at least 95% of red blood cells are retained in the bridging zone.

11. The method according to claim 2, wherein at least 95% of red blood cells are retained in the bridging zone.

* * * * *